United States Patent [19]

Barnes

[11] Patent Number: 5,583,432

[45] Date of Patent: Dec. 10, 1996

[54] ELECTRICAL METHOD AND APPARATUS FOR NON-CONTACT DETERMINATION OF PHYSICAL AND/OR CHEMICAL PROPERTIES OF A SAMPLE, PARTICULARLY OF BLOOD

[75] Inventor: Christopher Barnes, Bangor, United Kingdom

[73] Assignee: Sci-Nostics Limited, United Kingdom

[21] Appl. No.: 226,075

[22] Filed: Apr. 11, 1994

[51] Int. Cl.$^6$ .................. G01N 27/74; G01R 33/12
[52] U.S. Cl. ............................... 324/204; 324/232
[58] Field of Search .......................... 324/204, 232, 324/226, 262

[56]         References Cited

U.S. PATENT DOCUMENTS

| | | |
|---|---|---|
| 3,483,860 | 12/1969 | Namerow . |
| 4,135,131 | 1/1979 | Larsen et al. . |
| 4,257,001 | 3/1981 | Partain et al. . |
| 4,282,487 | 8/1981 | Warren et al. . |
| 4,563,644 | 1/1986 | Lenander et al. ............... 324/204 |
| 4,590,424 | 5/1986 | Girot et al. . |
| 4,965,206 | 10/1990 | Kell . |

FOREIGN PATENT DOCUMENTS

| | | |
|---|---|---|
| 0157496 | 10/1985 | European Pat. Off. . |
| 0309085 | 3/1989 | European Pat. Off. . |
| 2201762 | 4/1974 | France . |
| 2378282 | 8/1978 | France . |
| 3637549A1 | 5/1988 | Germany . |
| 3722213A1 | 1/1989 | Germany . |
| 595720 | 12/1947 | United Kingdom . |
| 1084860 | 8/1965 | United Kingdom . |
| 1018188 | 1/1966 | United Kingdom . |
| 1122922 | 8/1968 | United Kingdom . |
| 1460892 | 1/1977 | United Kingdom . |
| 1574681 | 9/1980 | United Kingdom . |
| 1599241 | 9/1981 | United Kingdom . |
| 2090431 | 7/1982 | United Kingdom . |
| 2115933 | 9/1983 | United Kingdom . |
| 2130728 | 6/1984 | United Kingdom . |
| 2248301 | 4/1992 | United Kingdom . |
| 2260407 | 4/1993 | United Kingdom . |
| WO85/04481 | 10/1985 | WIPO . |
| WO91/09295 | 6/1991 | WIPO . |
| WO91/15036 | 10/1991 | WIPO . |
| WO93/18395 | 9/1993 | WIPO . |

OTHER PUBLICATIONS

J. M. McKee, B. P. Johnson, P. F. Mastin and M. E. Fuller "Radiofrequency Finger Impedance Measurements", Proceedings of the Annual International Conference of the IEEE Engineering in Medicine and Biology Society, vol. 10, 1988, pp. 0761–0762.

Primary Examiner—Walter E. Snow
Attorney, Agent, or Firm—Spencer & Frank

[57]                ABSTRACT

A method and apparatus for investigating various parameters of biofluids, such as blood, particularly protein and cellular concentrations and cellular volume utilises the application of at least two a.c. frequencies, preferably simultaneously, in the range 0.1 to 60 MHz to a sample of the fluid and receiving and resolving the frequencies after passage through the fluid. The received frequencies are processed to derive corresponding d.c. voltage amplitudes which are mathematically processed to provide a numeric output correlating with a parameter under investigation, A new parameter named Instant Sedimentation Rate (ISR) is disclosed.

21 Claims, 10 Drawing Sheets

ELECTRICAL METHOD AND APPARATUS FOR NON-CONTACT DETERMINATION OF PHYSICAL AND/OR CHEMICAL PROPERTIES OF A SAMPLE, PARTICULARLY OF BLOOD

BACKGROUND OF THE INVENTION

This invention relates to a non-contacting apparatus and method for investigating certain properties of blood such as red cell count, haemoglobin and fibrinogen content, sedimentation rate and related physical and chemical parameters and for use with similar evaluations in other biological media and for more general use with other samples. In one example the invention is concerned with measurement of fibrinogen to establish instantly the expected sedimentation condition of red cells in blood and certain plasma properties.

Throughout, the term "non-contacting" indicates a means remote from and not in direct contact with the sample and the terms "instant" and "instantaneous" are used to indicate very near instant with process times only being limited by the speed of electron flow in circuitry, real time electronic calculation and the operation time of electronic display devices.

Protein concentration in biological media is usually assessed by biochemical methods or by methods of physical chemistry such as viscosity measurement and optical rotational dichroism. Also possible arc various forms of spectroscopic analysis and chromatography. In one specific situation, that of whole blood, the proteins with the highest concentration are haemoglobin, found in the erythrocyte nuclei and secondly fibrinogen, found dissolved in the plasma. Fibrinogen concentration is medically important, in that in excess it is a non-specific indicator of disease state in a person. Fibrinogen levels manifest their effects in a variety of different ways; firstly, they effect the sedimentation rate of the red cells (erythrocytes) giving rise to the so-called erythrocyte sedimentation rate (ESR) and secondly, they cause effect upon the physical and chemical properties of the plasma.

Manifestations of increased fibrinogen levels have traditionally been monitored in pathology laboratories by two tests, namely; the ESR and the plasma viscosity (PV); more recently a third biochemical assay, the so-called c-reactive protein (CRP) test has also become more popular. ESR tests are, however still the most popular with clinicians the world over. The ESR test traditionally uses about 5 milli-liters of venous blood and takes one hour to perform, during which time the red cell fraction (haematocrit) separates from the clearer plasma fraction and sediments slowly under gravity and subject to internal viscoelastic forces down a capillary tube or a. vacutainer containing preservative; this is very time-consuming. PV and CRP are also time-consuming and, because in these latter two tests, the red and white blood fractions have to be physically or chemically separate, there is always the chance, albeit remote, that the operatives might become exposed to viral or bacterial biohazard.

Other blood tests such as cell counting and sizing are also carried out in pathology laboratories using very expensive automated equipment which needs to sample small quantities of blood in close contact by sucking it through a needle type probe inserted by the equipment into a closed vacutainer. Such cell counters, sometimes referred to as haematological analysers, Coulter or similar cell counters, are extremely sophisticated and operate by application of non-linear electrical field gradients and voltage pulses across individual red or white blood cells which have been located by electric or hydrodynamic focusing in a narrow, micron sized, orifice or counting/sizing gate. These machines yield a myriad of parameters, up to 23 in some cases, about the state of nearly all the blood components. Nevertheless, they are non-portable and extremely expensive and limited by sample throughput and cleansing procedures.

Three of the most important parameters outputted by cell counters are perhaps the rod cell concentration (RBC), the mean cell volume (MCV) and the haemoglobin content (Hb). These parameters are considered very useful by many physidans in addition to the ESR value in order to make first diagnoses and general "state of health" assessments, and it would be useful if such parameters could be obtained by a simpler, cheaper, haematology or haematological analyser technology of greater portability, for use, for example, in medical practitioners offices, in the field, or in connection with third world applications.

Of these parameters, the problem of haemoglobin has been addressed by using optical technology and biochemical analysis of the erythrocytes. However, such technology is still quite expensive and because a chemical, reaction is involved there is a waiting time before the result is achieved, i.e. the output is not instantaneous.

Most matter is electrically and magnetically permeable to varying extends. The property, which influences electric fields or the electric field vector of electromagnetic waves (radiation) is the permittivity or relative dielectric constant $\epsilon$, while that with magnetic effect is the (magnetic) permeability $\mu$. Generally there are many more materials of low $\mu$ end a range of $\epsilon$, the so-called dielectrics, than there are magnetic materials of high $\mu$.

In dielectric laboratories, electrical properties of matter, especially liquids, are measured by bridge apparatus in which linear a.c. electric fields are employed end direct contact with metal electrodes is usually made. Alternatively, time domain pulse reflectometry is employed where the sample is housed in a metal cavity to form the termination impedance of a coaxial feed-line. These are standard techniques of so-called dielectric measurement.

The parameters obtained by such measurement are the frequency dependent dielectric parameters e', e" and tan $\delta$. These are often obtained for the sake of pure scientific research. Alternatively they may be mathematically or empirically related to, or are indeed characterized by, the physical and/or chemical state/properties of the sample. For instance, if the sample is a liquid containing particles in suspension, the size and number density of these may be hypothetically related to the dielectric parameters.

The haematological parameters of blood are manifold and complicated, in brief being related to the chemical and biochemical composition of the blood electrolytes and plasma and to the sizes and number densities of red and white cells and to the electrical charge states of their membrane surfaces and walls. Properties of blood and other cells are traditionally determined by Coulter apparatus in which individual cells are manipulated into a counting/ sizing dimension, manipulation and measurement often involving hydrodynamic focusing and the application of pulsed non-linear electric field gradients.

Coulter apparatus is extremely expensive, yet because of medical demand, is widely exploited. On the other hand, a system not in current commercial exploitation involves dielectric measurement of pathological blood samples to yield haematological parameters. Although academics have attempted to assess the dielectric properties of blood in the laboratory, it would seem, according to scientific literature that they have always employed pooled samples of cells of various mammalian species separated into individual red and white fractions, often suspended in artificial electrolyte media and always in contact with metal and employing the standard techniques described above.

Although there is a moderate amount of scientific literature on this type of approach, there is no really consistent agreement on the observed relaxation frequencies of mechanisms pertaining thereto. Indeed, serious errors of measurement can be introduced in test vessels where a liquid sample is contained in contact with metal for the purpose of dielectric measurement due to electrical double layer formation and electrode polarisation at the liquid metal interface and due to chemical reaction with aggressive chemical media, such as whole blood or blood fractions.

Recently, some new but relatively simple methods have been described for applying fixed frequency non-contacting dielectric (capacitive) measurements to flowing solids, e.g. fly-ash, as in UK patent application GB 2,115,933A, published on 14 September 1983. Similar techniques with vertically positioned, essentially parallel external electrodes forming part of a resonant LC circuit have been applied to the ease of flowing fluids, e.g. European patent application EP 0,309,085 A2, published 29 March 1989. However, such simple capacitive techniques effectively only measure the electrical permittivity in simple form, and only at a single frequency and not in complex frequency dependent form as referred to above, where:

$$\epsilon''(\omega)=\epsilon'(\omega)-j\epsilon''(\omega)$$

Because of this complex form, single frequency methods are strongly influenced by factors such as the D.C. ionic conductivity of liquid samples and/or the position(s) in frequency space, relative to the measurement frequency, of the dielectric loss maximum or maxima, and thus are not wholly satisfactory, particularly if a sample exhibits a multiple dielectric dispersion, of which blood is one such example.

It has also been recently recognised that the flow of electromagnetically permeable samples in tubes may be monitored by wrapping a non-contacting inductor around the tube and connecting it to essentially free running oscillator circuits so that either the self-resonant frequency of the inductor or resonant frequency of the inductor in series or parallel combination with a capacitor, crudely determines the oscillation frequency of the oscillator.

Alternatively, the coil may be driven with a.c. voltage in the region of parallel resonance and effective measurement of the Q-curve obtained by measuring the voltage across the coil. For dielectric samples, this procedure effectively measures non-complex, single frequency permittivity by its effect of dielectric loading and lowering of the Q of the coil, thus the above restrictions of two capacitor plate methods also apply. These very restrictions themselves, particularly with respect to low frequency dispersions or d.c. conductivity involving ionic conduction, and make the use of these methods suitable for some purposes such as detection of ion concentration in a liquid; see U.S. Pat. No. 4,590,424.

Similar inductive techniques have been applied to flowing particles where the predominant change in the coil is that of inductance rather than Q, the former being brought about by the particles significant magnetic permeability rather than simply dielectric constant alone. An example is European patent application 0,157,496 A2, published 9 October 1985. Whilst these wholly free running methods of oscillation are adequate for the purposes for which they have been employed they are not stable enough or sensitive enough for haematological purposes.

The material which is of prime concern for the present invention is blood, which has the potential to behave both as a dielectric and be magnetically permeable via the iron in the haemoglobin molecule. GR 1,574,681, granted to Labora Mannheim and published 10 September 1980 concerns one haematological aspect, namely time-dependent erythrocyte sedimentation. It employs either two electrode capacitive techniques or inductive LC techniques. Although a retuning mechanism is employed in assessing the sedimentation rate, the technique is still essentially a single frequency one, or at least the device operates within a single relatively narrow band of resonance frequencies about some mean which is not explicitly specified, and requires observations to be made over a period of time.

As with academic literature, patent literature seems to indicate that no attempts have been made to apply non-contacting dielectric methods for commercial exploitation in the haematological field for determination of standard haematological parameters other than time-dependent erythrocyte sedimentation rate. The other common hitherto dielectrically unexploited parameters include cell number density, size and haemoglobin concentration, usually referred to as RBC, MCV and Hb respectively. The present invention suggests that the restrictions on previous exploitations could be due to the general limitations of single two plate capacitor and single inductor methods as outlined above, particularly with respect to finite variations found with pathological blood specimens in plasma and electrolyte conductivity and due to the multiple dielectric loss mechanisms and maxima to be expected as arising from blood cell size, shape and molecular motions of the haemoglobin molecule and other protein and other molecules present in such pathological blood samples. It will be appreciated by those with knowledge in these fields that other fluids and materials both in vitro and in vivo could fall into this "restricted" category, i.e. subject to the same or similar limitations.

SUMMARY OF THE INVENTION

It is thus an object when of one aspect of this invention to provide a means to instantly assess blood fibrinogen levels and their related chemical and physical manifestations without direct contact and to be able to monitor, also without direct contact, any or all of the common red cell parameters referred to above, to help preclude biohazard and to provide an analogue or digital readout of all or any of these parameters, in devices that may or may not be configured as a simple form of haematological analyser, and an instant non-optical, non-cell counter means to determine MCV, and/or RBC and/or haemoglobin content of blood.

In the case of fibrinogen, it is also an object to provide an output which can be calibrated in units of concentration, or have units which are effectively dimensionless but whose numerical dynamic range scales and correlates according to any or either of the three common methods of fibrinogen assessment referred to above, or according to a new parameter which the present inventor chooses to refer to as ISR (instant sedimentation rate), but also accounting for and chosen according to the preference of the physician, etc.

Automated optical systems haw been tried for the assessment of ESR. these are not instant but they do, however, reduce the time required for a measurement down to about 20 minutes. Methods where the ESR tube is spinning in order to increase shear forces on the erythrocytes thereby speeding the rate are also possible.

Thus, it is a further object of the present invention to provide new, more advanced forms of non-contacting measuring cells, instant methods and apparatus for remote measurement on blood and other fluids based on dielectric principles where unlike the prior art and advantageously to it, there are provided either preferably two or more single, preferably non-varying (i.e. stable) frequencies that are simultaneously applied and employed or where if only one such frequency is applied then an external parameter will be required to be manually or automatically entered into the calculation circuitry to give a satisfactory result hitherto not instantly available by other methods of the prior art.

It is a further object to provide new kinds of inductive measurement cells and methods and apparatus for applying the above said frequencies, not hitherto described in the prior art.

According to the invention, a method for investigating one or more parameters of biofluids, particularly blood in respect of protein and cellular concentrations and cellular volume, comprises the steps of applying to a sample of the biofluid, and without direct contact with the sample, at least two a.c. frequencies in the range 0.1 to 60 MHz, simultaneously receiving and resolving the frequencies after their passage through the fluid, obtaining subsequent d.c. voltage amplitudes by detection of the received and resolved frequencies, thereafter applying mathematical processing to the d.c. voltage amplitudes to provide a numeric output which correlates with at least one of the parameters.

Preferably the two frequencies form a pair within a recognised frequency dispersion, wherein at least one of the frequencies is close to the maximum amplitude of the dispersion.

Preferably both of the frequencies offset to the same side of the peak frequency.

The invention further resides in apparatus for investigating one or more parameters of biofluids, particularly blood in respect of protein and cellular concentrations and cellular volume, comprising a measurement cell for containing a sample of the biofluid, means for applying at least two a.c. frequencies in the range 0.1 to 60 MHz to a sample of the biofluid within the cell and without direct contact with the sample, means for receiving and resolving the frequencies after passage through the fluid, means for obtaining d.c. voltage amplitudes by detection of the received and resolved frequencies, and means for applying mathematical processing to the d.c. voltage amplitudes to provide a numeric output which correlates with at least one of the parameters.

The means for applying and receiving the frequencies may be arranged externally of the cell or be disposed within a probe which is inserted into a sample in the cell.

Accordingly then the present invention consists of in one aspect, apparatus for determining the physical and/or chemical properties of a sample, blood or other, with means for retaining the sample, means remote from the sample for applying at least one frequency to the sample, means for measuring the magnitude of the dielectric properties of the sample at each of the the frequencies simultaneously and means for correlating the required physical and/or chemical property of the sample from a simultaneous comparison of the magnitude of a dielectric property of the sample at one of the measuring frequencies with that at the other measuring frequencies or with an alternative parameter proportional thereto.

Furthermore accordingly, the the apparatus of this invention consists of non-contacting, dielectric measurement cells linked to electronic circuitry through which external parameters can be entered if necessary.

Accordingly, the method involves inserting and retaining samples, blood or other, in the apparatus, applying the frequencies, measuring the magnitudes and correlating the required physical and/or chemical parameters, and providing a scaled readable analogue or digital output by means of internal electronic (calculating) circuitry. Often one, two or four frequencies are applied.

In the case of two frequencies, one may be between the dielectric alpha and beta dispersions and the other on the high side of the beta dielectric loss maximum, whereas in the case of four frequencies all may be on the high side of this beta loss maximum. The method is ideally suited for assessing protein and cellular concentrations in blood and other biofluids, but use of other samples is not ruled out.

Protein concentration is assessed by its effects on the position and/or magnitude of the high frequency tail of the beta dispersion.

Furthermore, as a component of some of the measuring cells available to the apparatus, there are provided circumferential electrode structures, spaced lengthwise on a former which is electrically insulating and may double as a tube with one, both, or no ends open, into which the separately insulated open or sealed sample robe might be pushed.

Furthermore and advantageously, measurement is made either by monitoring the voltage on the transmitting electrode, the receiving electrode or both, previous inventors have only monitored the voltage on a receiving electrode, or used the capacitance of electrodes to resonate in parallel with an inductor, to tune a variable frequency oscillator.

In another aspect of the apparatus and method, structures as those referred to above are employed, but assessment is of the number density of red cells by measurement at frequencies in kilohertz regions, and assessment of near cell volume in blood is also made with frequencies in the low megahertz regions.

In another form the present invention employs structures as above, but a single frequency is used in conjunction with an electronic circuit which uniquely and advantageously allows temperature compensation and entry of an external parameter such as haemoglobin content from another source such as a cell counter or optical haemoglobinometer if the sample is blood, in order to provide a more precise output of fibrinogen content, or fibrinogen related parameter(s).

In another form the present apparatus and its non-contacting cells are used for assessing changes in the conductivity and/or dielectric constant of a medium under physical or chemical change e.g. chemical reaction, bioreaction, biochemical or biotechnological reaction, by following the temporal evolution of the output parameter.

In a further form the present apparatus is used for any of the uses referred to above, but the electrode structures are replaced by a single coil or inductor wound around and lying in the plane of the former and where the coil via its effect upon a crystal controls the frequency and amplitude of a variable crystal oscillator by series inclusion in the input oscillating tank, not output load and not feedback, circuit. Advantageously such a method is inherently far more stable than those employing free running types of oscillator. Since output frequency of a variable crystal oscillator can be measured by a counter very accurately, down to fractions of a Hertz, there is thus, concurrent with the increased stability referred to herein an increased precision and sensitivity over other methods.

In a further aspect of the present invention, a coil structure surrounds the apparatus measuring cell and the coil (inductor) has a low impedance tap or link into which power is fed via a coaxial line from an exciter. Any of the assays and samples mentioned herein may be measured with the invention configured in this way, since the properties of the sample are mathematically or empirically related to the voltage standing wave ratio on the coil line as measured by a reflectometer or voltage standing wave reflectometer (VSWR) in that line, provided with or without further d.c. amplification.

Yet a further aspect of the present invention is a two frequency measurement cell, method and device, in which a central former is surrounded by four coils or inductors lying coaxially (circumferentially) around it, evenly or not evenly spaced, two of which are non-resonant input (transmit) coils, each sending in a separate single frequency, and two of which receive singly and separately, yet simultaneously, the original frequencies after passage through the former walls and sample.

A further aspect of the present invention includes operation as per the electrode based two frequency method described earlier, but where a signal recovery technique is employed on the low frequency receive electrode which consists of a high Q ferrite cored inductor connected from the electrode to earth which resonates with the electrode self-capacitance, thereby boosting the recovered low frequency signal. This is advantageous because otherwise signals of kilohertz frequencies would suffer very great attenuation after passage through the high impedance of the former and sample holder walls and would thus be virtually undetectable but for this aspect.

Those skilled in the art will appreciate that other signal recovery methods such as radio frequency amplifiers and/or phase-locked-loop techniques could also be employed in this context within the scope of the claims of this invention.

It is an observation of the present inventor that the dielectric (capacitive and conductive) facets of a pathological blood sample measured at individual frequencies in the range 10 KHz-1 GHz are related to the general state of health of the individual from which the sample was acquired. Thus it is yet one further aspect of invention to provide an electronic general health status indicator based on the observation that there are "norms" of dielectric response at each frequency in the radio frequency continuum and that this can be used with and may contain any of the aforesaid or following aspects of the present embodiment.

It is believed that these "norms" arise due to the combined effect of RBC, MCV, Hb, various other proteins, cell membrane leakiness and plasma electrolyte strength upon the loss peak maxima magnitudes and positions in frequency space of the double or multiple dielectric Beta dispersion of blood, with these dispersive phenomena lying in the approximate frequency range 0.1–60 MHz.

In yet a further form, the invention, in any of its previous embodiments, consists of cells, methods, means and devices capable of measuring, without contact and without the use of optics, some of the physical dimensions and dielectric properties of sample containers, should these vary from container to container if the containers are filled with fluid of constant chemical and physical composition and dielectric property.

In a final aspect of this invention, any of the measuring cell methods, and apparatus referred to herein as belonging to this invention may be operated in a differential mode, i.e. using two identical sets of the cells, devices or apparatus, with the sample being placed in/measured by one member of the set and a dummy sample, containing for example air, water or electrolyte etc.; and being placed in/measured by the second member of the set. By employing identical components, mechanical and electronic, in each of the the sets, and then connecting them to a differential output stage, this aspect of the present invention allows for the provision of improved results as environmental effects, such as temperature, will tend to be cancelled by the differential stage.

Although the invention and all its embodiments described herein are primarily illustrated as device(s) for determining protein and cellular concentration in liquids, preferably whole blood without contact, it is not intended to be limited to the precise detail shown, since various modifications could be made therein within the scope of the appended claims.

BRIEF DESCRIPTION OF THE DRAWINGS

The invention and some of the advantages thereof will now be described more fully by way of reference to the accompanying drawings in which.

DETAILED DESCRIPTION OF THE PREFERRED EMBODIMENTS

Figure 1:
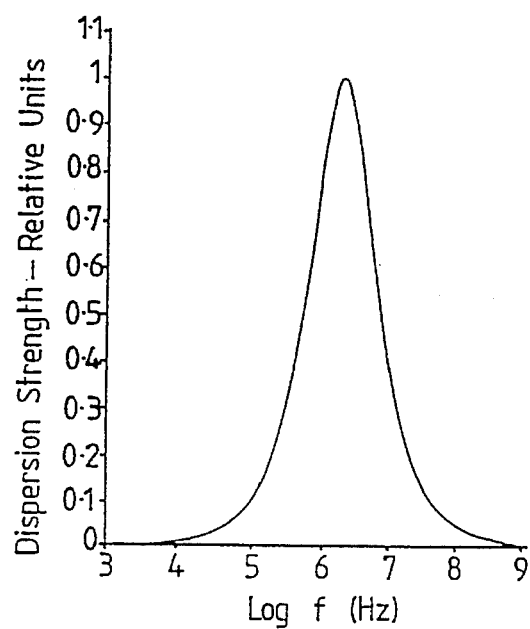
FIG. 1 shows a theoretical frequency distribution for a typical dispersion plotted on a log scale.

Dielectric measurements have been made on mammalian blood cells in artificial suspension media over several decades. The erythrocytes used have generally been washed (i.e. separated from plasma centrifugation, re-suspended in buffered isotonic saline and re-centrifuged) and finally re-suspended in buffered solutions with additives to prevent sedimentation. There appear to be no reports of dielectric measurements on whole blood samples from human patients with different disease states.

Dielectric measurements have been made with cells in contact with electrodes using AC bridge techniques, and more recently with time domain spectroscopy.

As long ago as the 1930s it was established that there were two strong dielectric dispersions associated with blood and other biological tissue, the alpha and beta dispersions. Alpha dispersion is associated with the tangential relaxation of ions adjacent to cell surfaces and the beta dispersion is due to membrane charging capacitance.

The alpha dispersion ranges from a few Hz to about 20 kHz.

The number of "close ions" (that is the ions associated with membrane through electrostatic interactions) will depend on the number (more properly the concentration in a fixed volume) of cells in suspension if the zeta potential is assumed to be constant. This may be a possible route to cell counting.

The beta dispersion ranges from about 20 kHz to 20 MHz.

The beta dispersion could be used to calculate factors such as cell membrane capacitance, width of the cell and cytoplasmic conductivity, The theory of beta dielectrics was used to support Maxwell-Wagner theories for the structure of mammalian cell membranes as lipid bilayers, and could be used to predict the thickness of the bilayer when appropriate values of dielectric constant expected in the three relevant regions (inside and outside electrolytes, and the membrane) were inserted into the relevant equations.

It was also realised that the value of the relaxation time (Tau) of the beta dispersion is a function of the volume of the cell. Cells that depart from sphericity (with ellipsoidal or oblate shapes) display a beta dispersion in the same frequency range, but the frequency may be dependent upon the axial ratios.

The present invention uses the beta dispersion for the mean cell volume (MCV) measurement.

There also exist other dispersions with lesser strength than alpha and beta dispersions. Such dispersions, reported recently for blood and biological materials have great significance for the present invention. Macromolecular material within the cell may broaden the high frequency tail of the beta dispersion in the region of 20 MHz. This has been recognised as a dispersion in its own right, and has been variously named the beta-1 or delta-2 dispersion. This dispersion is of importance in haemoglobin (Hb) measurement.

Furthermore, another dispersion, the delta-1 (or delta) dispersion is another weak dispersion and extends from about 50–500 MHz. It is believed to be due to rotational and other motions of side arms of proteins and macromolecules, and is not exclusive to intracellular material. Since it is a measure of total system protein content it is highly relevant to the success of the present invention for measurement of "instantaneous sedimentation rate" (ISR) as herein defined.

Finally, rotation of smaller molecules and bound cytoplasmic water occurs at higher frequencies of 1–10 GHz before the system is said to be totally relaxed out.

Measurements made in accordance with the present invention depend upon the dispersions beta (for MCV), beta-1 (for Hb) and delta (for ISR) and the precise positions of their absorption maxima (characteristic frequency). The dispersions are broad, and therefore tend to overlap. This means that, in effect, a variable DC level exists because the variable cell count will affect the alpha dispersion. In addition, plasma DC conductivity may also be of relevance to the precise DC magnitude of later dispersions. The precise positions of the characteristic relaxation frequencies in frequency space are unlikely to be affected.

In simple terms, dispersions which are to be measured occur on an underlying background of varying DC level which affects the magnitude but not the frequency position of the signals.

The techniques encompassed by the present invention are required to extract the quantitative information that depends upon the position of a characteristic frequency in frequency space for each measured parameter. Clearly, measurement of magnitude at a single frequency to assess the different parameters will not be possible because of the varying DC component. However, the quantitative information is still assessable by ratioing values at a pair of frequencies, the results of the ratioing technique correlating with laboratory results. This mathematical relationship is described in detail later. It is this ratiometric measurement, in combination with the multifrequency interrogations of the sample which allows the apparatus in accordance with the invention to function. Methods that are not dissimilar are used in chromatography to evaluate mounts of eluting materials against a varying background.

The MCV measurement depends upon the characteristic frequency of the beta dispersion being proportional to the reciprocal of cell size. For a spherical cell with a radius of 3 microns, the appropriate frequency is 5.3 MHz. In good agreement, the long axis of the human erythrocyte, 7 microns, yields an experimental maximum dispersion at 2 MHz. In general, relaxation frequencies given by a full ellipsoidal formula are very close to those of spherical cells.

Human MCVs are generally in the range of 60–100 fL. The ratio of the maximum over the minimum volumes is 1/0.54, which yields a ratio of radii of 1/0.83. If the minimum characteristic beta frequency is 2 MHz, the maximum will be about 2.4 MHz by calculation.

There is strong experimental evidence to support this, and the frequencies used in the apparatus in accordance with the invention may typically be 1.7 and 2.4 MHz.

The Hb measurement makes use of the beta-1 dispersion, and the peak dielectric loss for free oxyhaemoglobin molecules in solution bas been shown to be at about 10 MHz. In this case two frequencies are positioned at 16 and 20 MHz, that is on the high frequency side of the maximum relaxation. The reason for this is that although the maximum relaxation frequency should not shift significantly, there is some experimental evidence that it can move to somewhat lower frequencies as Hb concentrations increase. This shift forms the basis of the Hb measurement.

There also exists a theoretical model that predicts a similar behaviour in the case of a dispersed spherical component in a dielectric mixture. Hb molecules could be considered as dispersed spherical molecules within the intracellular fluid.

The ISR measurement, i.e. the Instant assessment of the erythrocyte Sedimentation Rate (ESR) makes use of the Hb measurement and the total protein content obtained from the delta (or protein UHF dispersion). The magnitude of the delta dispersion amounts to approximately 0.4 dielectric units per 1 g/dL of protein. Subtraction of the Hb concentration leaves a measure of the total protein in the sample mainly the plasma protein. Of the plasma proteins, fibrinogen has a very large molecular weight, and also the greatest concentration variation (together with the gamma globulin fraction). The traditional ESR value depends strongly upon changes in fibrinogen and gamma globulin fractions; these proteins affect rouleaux formation of erythrocytes and plasma viscosity, hence the sedimentation rate. The fibrinogen and gamma globulin fractions will be expected to dominate the relative sample-by-sample loss changes.

The ISR measurement is a measurement of the concentrations of the proteins that affect ESR, and a strong correlation between the two parameters is believed to exist.

The mathematical basis establishing the validity of ratiometric measurement is as follows.

According to Debye for a situation where equilibrium is attained exponentially over time when a constant external field is imposed on a dielectric, the complex permittivity consists of a real and imaginary component $\epsilon'$ and $\epsilon''$. In its simplest form the current technology actually measures a complex combination of both components (however these are separable if phase sensitive detection is employed as mentioned above). It is easiest to envisage the imaginary component $\epsilon''$, which is given by $$\epsilon'' = (\epsilon_s - \epsilon_\infty)\omega\tau/(1+\omega^2\tau^2)$$

where $\tau$ is the relaxation time in seconds and $\omega$ is the angular frequency $2\pi f$.

Let $(\epsilon_s - \epsilon_\infty)2\pi = \alpha$ and $\omega = 2\pi f$

Then the equation can be restated as:

$$\epsilon'' = \alpha f \tau/(1+4\pi^2 f^2 \tau^2)$$

It has been noted that for a single Debye type relaxation process, the width of the $\epsilon''$ peak at the half-height value is 1.14 decades in frequency and the transition from low frequency to high frequency dielectric behaviour is approximately over the range of four decades in frequency.

Applying the above to a frequency range of 0 to 10 MHz with an amplitude normalised to unity at 2 MHz (typical for MCV measurement) allows the equation to be solved for $\alpha$ and $\tau$.

The solution gives values of:

$$\alpha = 2.000408 \text{ and } \tau = 0.7799 \times 10^7$$

FIG. 1 shows the distribution plotted on a log scale.

Figure 2:
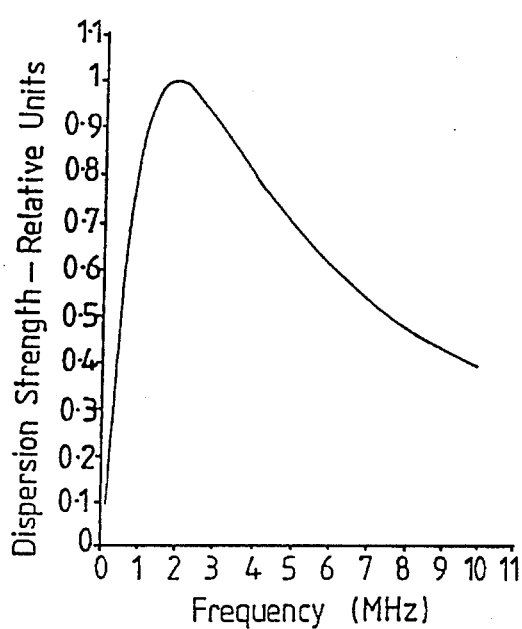
FIG. 2 shows the distribution of FIG. 1 plotted on a linear scale to simulate a typical situation in measurements in accordance with the invention.

FIG. 2 shows the distribution plotted on a linear scale simulating the method of measurement employed in the present invention.

The other important point to be considered is the effect upon this distribution of the underlying equivalent d.c. level arising from the influence of other dispersions and the d.c. conductivity of the sample.

Dielectric absorption is a measure of the energy dissipated in the medium and therefore processes which are usually related to the d.c. conductivity can also contribute to the total dielectric absorption. In addition to this influence then amongst other parameters, the $\beta$ dispersion of the measured component can be influenced by an equivalent "d.c." level caused by the low frequency tail of higher frequency dispersions and by the high frequency tail of lower frequency dispersions arising from other components in the system.

The total dielectric loss $\epsilon'_\tau$ at a frequency of f is given by $$\epsilon''_\tau = \epsilon'' + \sigma/2\pi f \epsilon_o$$

It can be seen from this that the d.c. level can contribute significantly at low frequencies but becomes progressively less influential as frequencies increase. For blood, $\sigma$ is of the order of $10^{-2}$ and $\epsilon_o$ of the order of $10^3$. Therefore, at a frequency of 2.0 MHz the loss due to d.c. conductivity is of the order of $10^{-11}$ and is therefore negligible.

However, it is recognised that other influences (e.g. tangential relaxation of the ions at the cell surfaces, i.e. the a relaxation) can contribute to the d.c. level and it has been found empirically that the maximum point moves on the y-axis and rotates around this new maximum, i.e. relaxation frequency does not change. Potentially, there is likely to be a widening of the curve for reductions in amplitude and a narrowing for increases as the area under the curve, representing the energy level, must stay constant. It has been shown experimentally that the contribution from d.c. conductivity is insignificant and therefore allowing a change of 0.1 on an amplitude maximum of 1 provides a scenario of significant impact in simulating a worst case scenario for the ratiometric method of measurement.

Applying the equation for total dielectric loss shown above to this scenario gives a value of $2 \times 10^5$ for the constant $\sigma/2\pi\epsilon_o$ applied to the reciprocal $1/f$. It has been suggested that the relaxation frequency is linearly proportional to $1/r^3$ and therefore the theory supports the observation that for varying values of the measured parameter, the distribution moves linearly along the x-axis.

Figure 3:
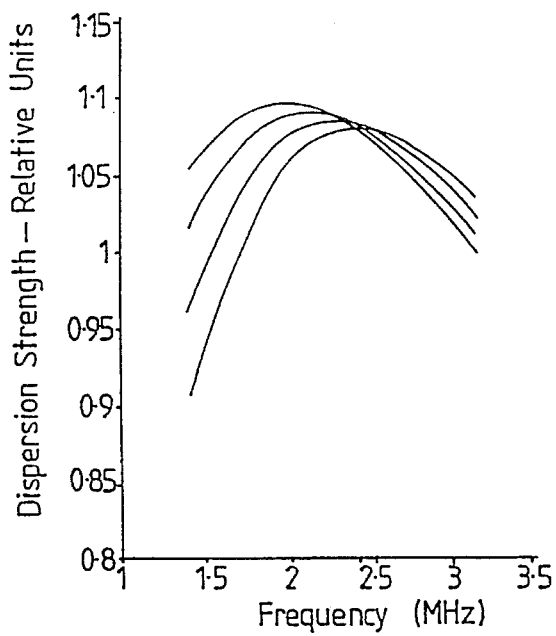
FIG. 3 illustrates shifting of such frequency distribution resulting from extraneous d.c. levels.

FIG. 3 illustrates this phenomena for four shifted frequencies.

Figure 4:
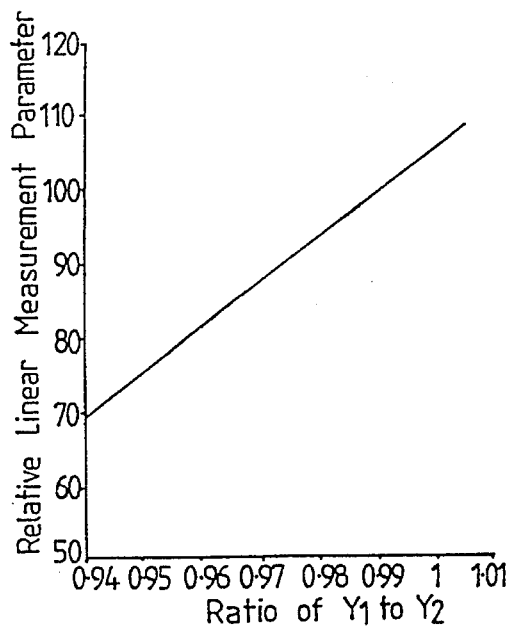
FIG. 4 shows the linear regression analysis for values adjusted on the selected frequency for d.c. levels.

It has been established by the present inventor that the frequency pairs necessary to provide accurate measurement need to be on the same side of the peak frequency and close to the maximum amplitude. Selecting frequencies 1.7 and 2.4 MHz meets these criteria and gives four $y_2:y_1$ ratios. FIG. 4 shows the linear regression on these ratios. This gives a maximum variance across the range of 2.33%. This is well within the limits set for the accuracy of the measured parameter.

In summary, the ratiometric method gives an almost perfect linear relationship to the measurement parameter under investigation even allowing for a significant shift in d.c. level and provided that one of the paired frequencies is close to the maximum and ideally the other is on the same side of the curve.

In the case of MCV measurement the low frequency side of the curve is employed so as to minimise the influence of the Hb dispersion, and in the case of Hb measurement, the high frequency side is used to minimise the influence of the MCV dispersion.

Figure 5:
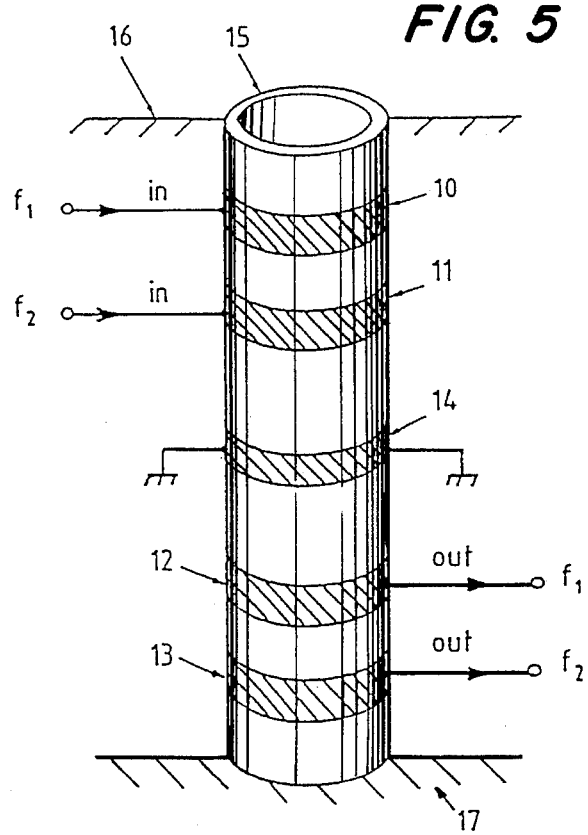
FIG. 5 illustrates a two frequency measurement cell, with an insulating former and outer annular (circumferential) electrode structure for use in this invention.

Referring to FIG. 5, in a two frequency measurement cell, circumferential transmit electrodes 10 and 11, remote from the sample, are usually, although not exclusively, fabricated from thin brass shim on the outside of a former 15. Frequencies $f_1$ and $f_2$ are simultaneously passed into electrodes 10 and 11, and are simultaneously recovered from two similar receiving electrodes 12 and 13. A central grounded electrode 14 is provided to minimise stray signal leakage along the surface of former 15. Earthed ground-planes 16, 17 minimise r.f. radiation from the cell.

Figure 6:
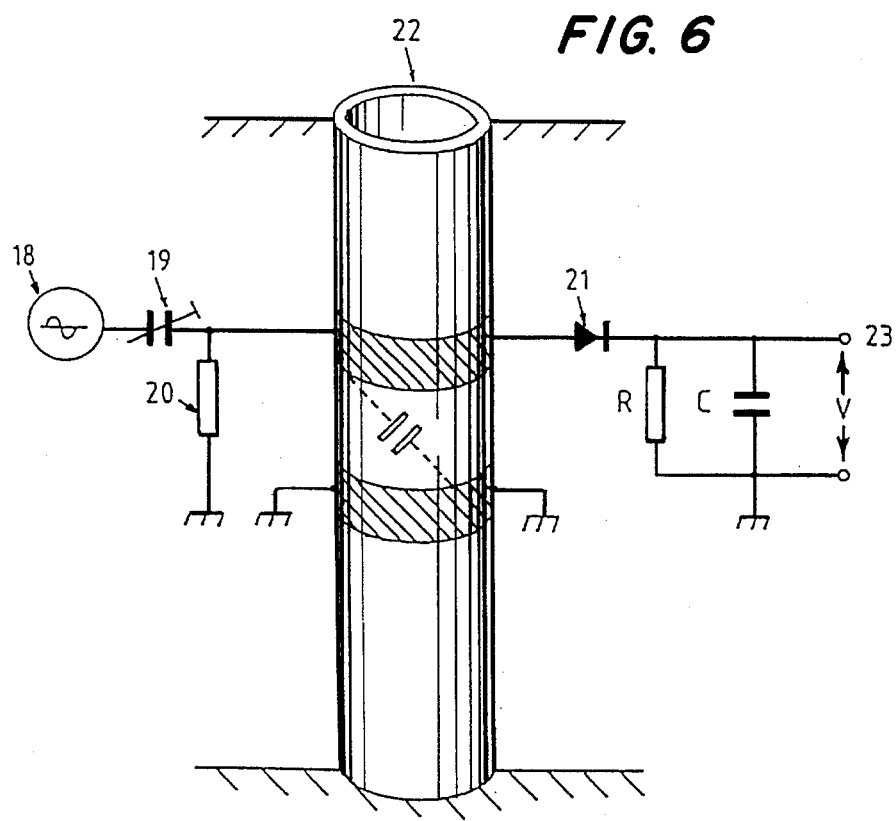
FIG. 6 illustrates a method of monitoring voltage at the transmit electrode in this invention and shows the stray capacitance path to earth.

Referring to FIG. 6, the method of measuring voltage at the transmit electrode 18 is a crystal controlled oscillator or similar stable exciter. A 5 picofarad (or thereabouts) trimmer capacitor 19, a resistor 20, usually although not exclusively in the range 5–25 k ohms, and a signal diode 21 are connected as shown. This method has the advantage that detection is made at a relatively high r.f. voltage. Capacitor 19 and resistor 20 adjust the effective impedance at the transmit electrode to a value which is easily influenced or changed by introduction of a sample tube containing blood or similar into the orifice 22. This change occurs due to leakage of the signal to earth and the impedance at the transmit electrode being too high to sustain constant current flow. Thus the voltage on this electrode will fall when a sample is introduced. Terminals 23 are thence connected to an electronic voltmeter for interpretation.

Figure 7:
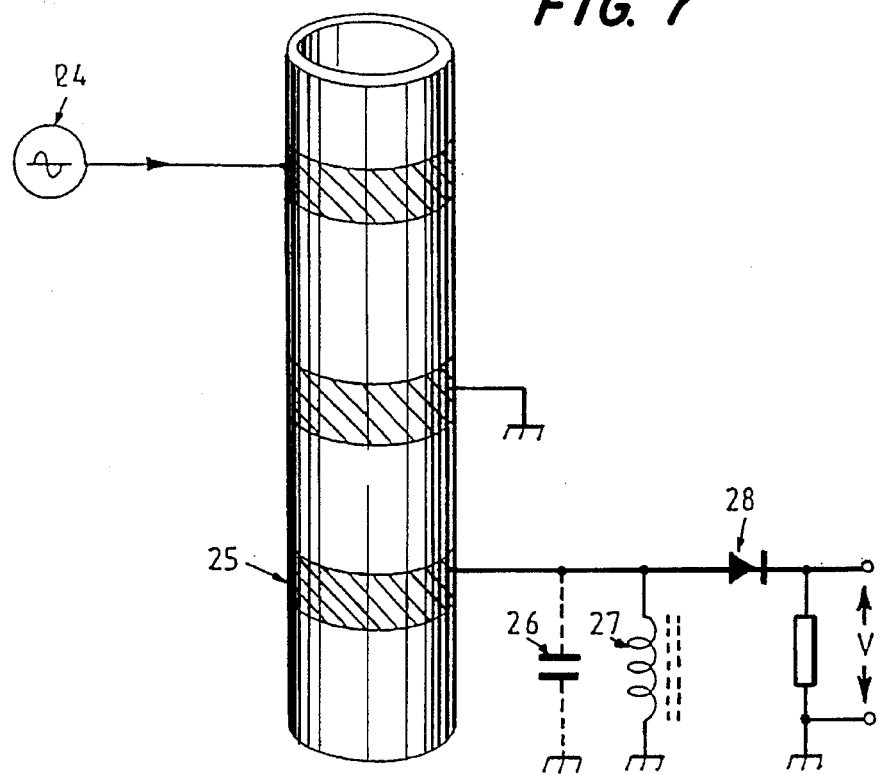
FIG. 7 is a diagram illustrating a method of signal recovery, for boosting kilohertz signals after passage through the former and sample.

Referring next to FIG. 7 a method of signal recovery for kilohertz frequencies employs a kilohertz frequency generator 24, typically though not exclusively, operating at 160 kHz sine-wave and a receiving electrode 25, whose self-capacitance 26 brings about high Q resonance, with a ferrite cored inductor 27 in order to boost the recovered signal appearing for detection at 28.

Figure 8:
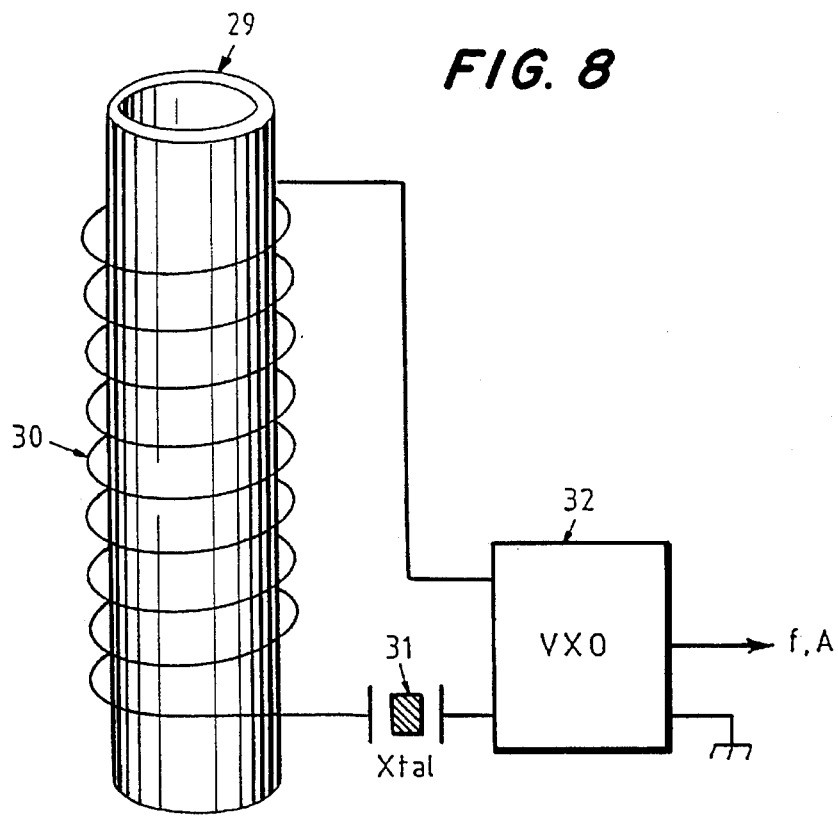
FIG. 8 is a diagram of an alternative measurement cell with an inductor connected to a variable crystal oscillator, for use with this invention.

Reference to FIG. 8 shows an alternative measurement cell and single frequency variable crystal oscillator (VXO) method used with this aspect of the present invention. Coil 30 is wound around former 29 and is connected in series with crystal 31 to form the input tank circuit of VXO 32. The output frequency and amplitude of VXO 32 will differ when former 29 is empty and when former 29 contains a sample in its own tube. They will also differ from sample to sample and will drift if any of the sample properties is temporally unstable. Thus physical and chemical properties of sample may be related to amplitude and frequency of VXO 32. This method is superior to those which have used a VCO due to an inherently higher stability of a VXO, and is superior to those which have used a coil in a feedback circuit or crystal oscillators for simple on/off bang/bang control.

Figure 9:
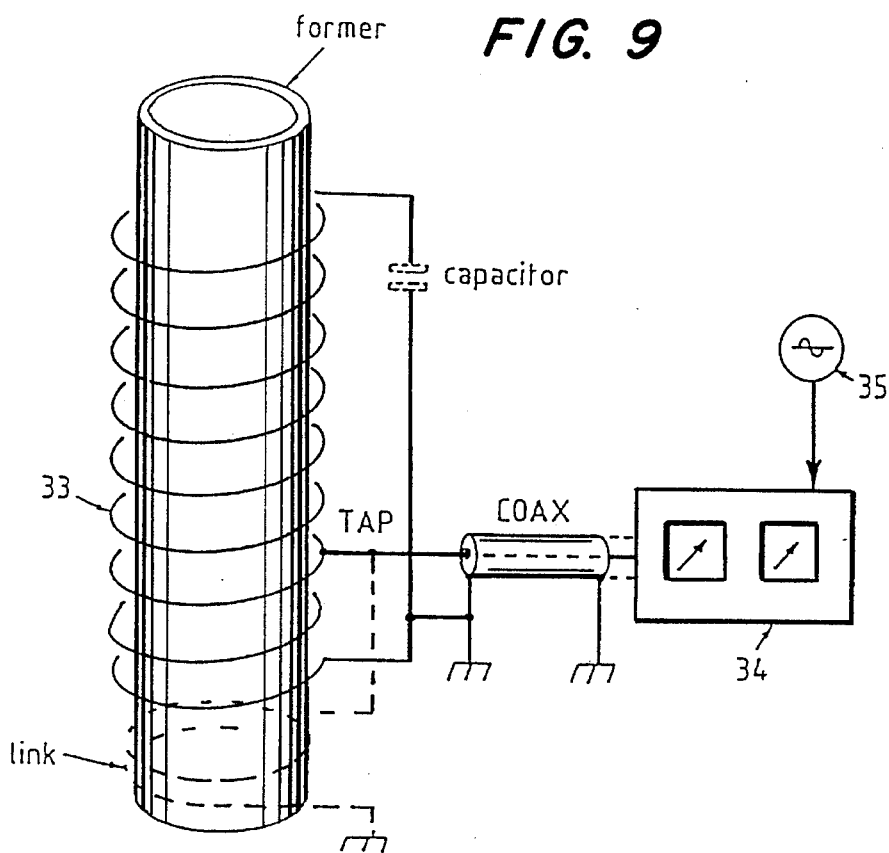
FIG. 9 is a diagram of a measurement cell, former, tapped coil anal device showing manner of connection to voltage standing wavemeter (reflectometer), according to this invention.

FIG. 9 shows a continuous wave voltage standing wave reflectometer (VSWR) method where an inductor 33 with a low impedance tap point or a link resonates with a capacitor, either self capacitance of inductor and former or external additional parallel capacitance. Power is fed into inductor 33 from exciter 35 via reflectometer or voltage standing wave meter 34. Meter 34 may or may not require d.c. amplification. When a sample tube is pushed into the orifice of the former 29, the resonant frequency of the system alters slightly, causing an alteration in the amount of power absorbed by the inductor 33 and reflected back towards exciter 35. The change in this reflection or VSWR is sensed and measured by meter 34. Thus, the reading of meter 34 relates to physical and chemical properties of the sample, including temporal instability of a sample.

Figure 10:
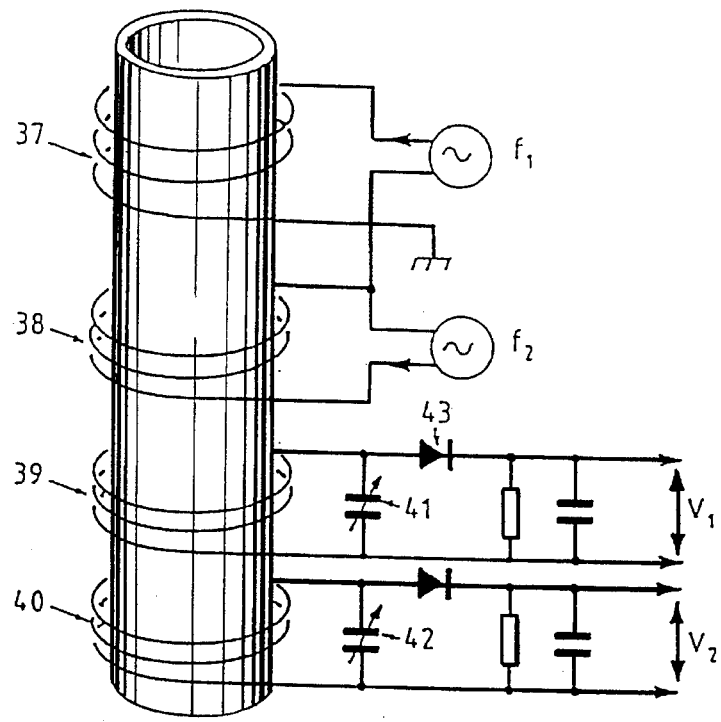
FIG. 10 is a diagram of a two frequency four coil measurement cell according to this invention.

FIG. 10 shows an inductive variant of FIG. 5 in which a two frequency four coil measurement cell is used. Power is passed in at two frequencies $f_1$ and $f_2$ simultaneously by non-resonant link inductors 37 and 38, respectively. These frequencies are recovered after passage through the former, sample tube and sample by resonant recovery at parallel tuned circuits 39/41 and 40/42. Any chosen degree of mathematical comparison, calculation or processing then follows on the voltages $v_1$ and $v_2$ depending on the precise application and sample type.

Figure 11:
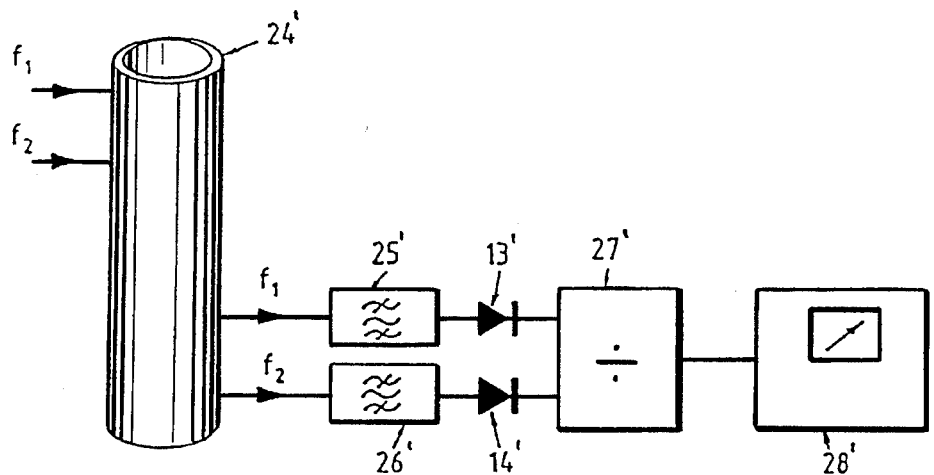
FIG. 11 shows the block diagram of a device suitable for measuring mean cell volume or haemoglobin calculation in blood samples.

FIG. 11 shows how the cells and methods described previously with reference to FIGS. 5 and 10 may be employed to form a device to calculate, without direct contact, the erythrocyte mean cell volume (MCV) or haemoglobin concentration of a blood sample, preferably though not necessarily exclusively, within a citrated vacutainer. In the case of MCV measurement, the vacutainer is inserted into the orifice formed by the former 24' which has four separate coils as described in relation to FIG. 10. In this case the specific frequencies chosen are $f_1$=2.45 MHz and for $f_2$=1.742 MHz, although the other pairs of frequencies in the range 100 KHz - 4 MHz are not ruled out. Narrow band band-pass filters 25', 26' are centred on $f_1$ and $f_2$ respectively.

Detectors 13' and 14' feed a real time computational circuit 27' which performs a division function, $f_1f_2$, and in turn drive an analogue or digital display module 28'. The blood MCV value is outputted at this module.

Returning to the aspect of two frequencies, these are employed primarily in the case of blood MCV in order to eliminate d.c. conductivity effects which will be cancelled in the division function, as will tend also to be, all lower and higher frequency dispersions away from the one of interest, i.e. that closest $f_1$ and $f_2$. on the basis of their lower slopes in terms of their own individual components of $\epsilon$ versus frequency relative to the mean frequency window established by $f_1$ and $f_2$.

Furthermore in the MCV case, the precise choice of $f_1$ and $f_2$ and their window in frequency space specifically helps reduce contributions from the higher low frequency haemoglobin dispersion, the dielectric loss per wavelength of which at least for pathological blood samples in titrated vacutainers appears to peak in the region 5–15 MHz.

In the case of using the FIG. 11 device, for haemoglobin calculation, similar principles to those established above for MCV apply except the two frequencies $f_1$ and $f_2$ are chosen well beyond the MCV dispersion and inbetween the l.f and h.f. haemoglobin dispersions. In one specific case, frequencies of 28 MHz and 40 MHz are employed, but once again the choice of other nearby frequency pairs is not ruled out, such as 16 and 20 MHz. Also for haemoglobin ceil 24' becomes the five electrode measuring cell of FIG. 5. With cell 24' in this configuration, the filters 25', 26' are preferably multipole quartz crystal or mechanical filters with pass frequencies of 28 MHz and 40 MHz. The haemoglobin value is then obtained by division of the d.c. signal from detector. 14' by that equivalent d.c. signal from detector 13' in real time computational circuit 27'. The output may be either analogue or digital but included in the output module drive circuitry are range d.c. offset and gain/range expansion features in order that module 28' can output Hb in internationally recognised units. Similar features in respect of gain and offset arc also provided in the MCV case above. Those skilled in the art will appreciate that the 40/28 MHz two frequency system will also work with electrodes in contact with the blood if blocking capacitors are employed.

Figure 12:
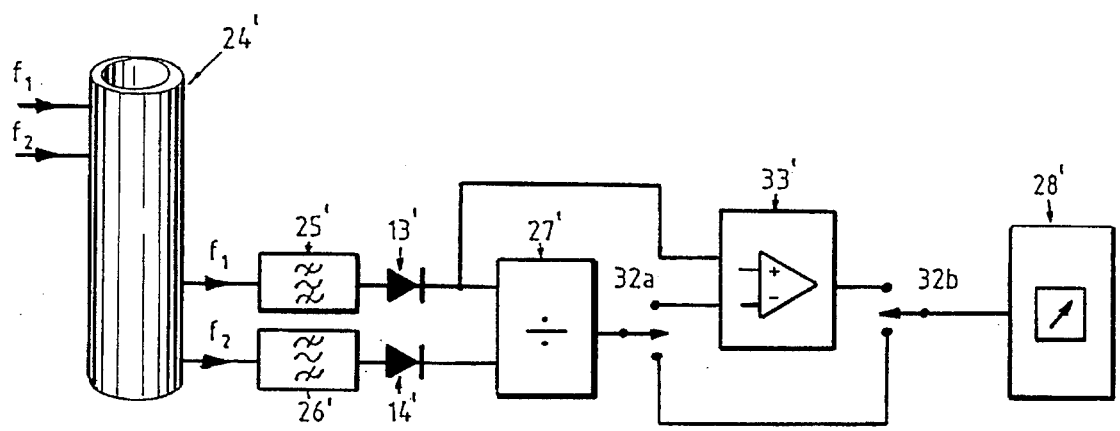
FIG. 12 shows the block diagram of a device for simultaneous automatic haemoglobin and ISR measurement.

With further reference to the drawings, FIG. 12, indicates that there is a device that can calculate both Hb and ISR simultaneously. In essence the, bulk of the operation of this device is as that discussed earlier for Hb alone, i.e. the device in FIG. 11. The Hb is calculated in exactly the same way as before but may be electronically routed by switch 32a and 32b between either the display 28' or a further differential circuit 33' which compares it with the d.c. voltage from the 40 MHz detector and thus produces an ISR output. The display 28' may be toggled freely between Hb and ISR. Alternatively, two simultaneous displays may be utilised. Those skilled in the art will appreciate the system can work by making contact as well as without contact. It will be appreciated by those skilled in the art that use of higher frequencies in the range 200 MHz-10 GHz in relation to the above two embodiments is not ruled out, but obviously is technologically more challenging. All comments made in respect of electronic variants to the cells and methods in the first embodiment of the invention also apply where those cells and methods are utilised in devices of the second embodiment.

Figure 13:
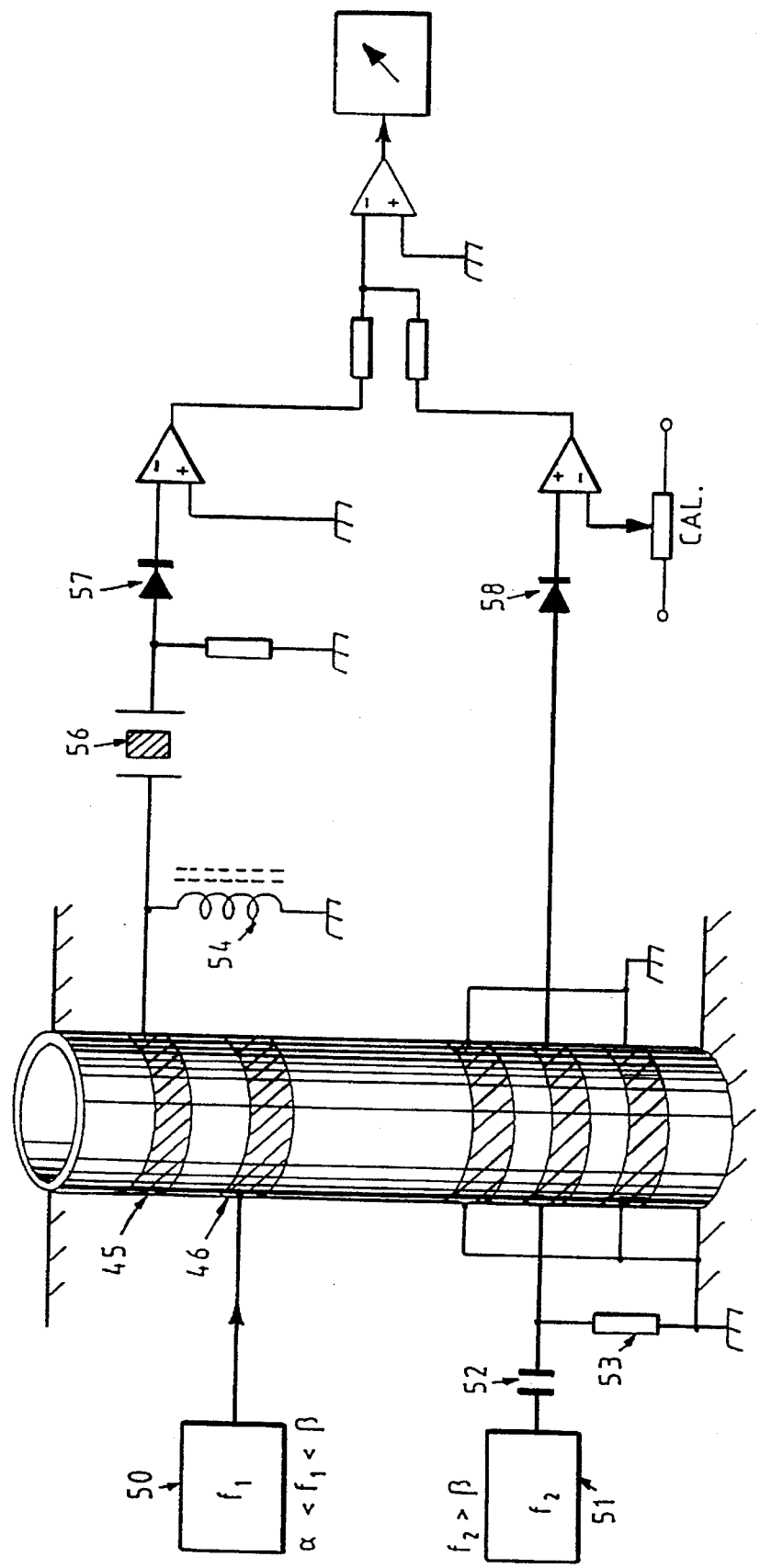
FIG. 13 illustrates a block diagram of a two frequency method and device for the measurement of protein, preferably fibrinogen in blood, which device can also be used to measure red cell concentration and/or cell volume by appropriate adjustment of frequency pairs according to this invention.

Reference to FIG. 13 shows a specific use of the invention as a device in block diagram preferably for the measurement of fibrinogen in blood. Frequency $f_2$ is on the high frequency tail of the dielectric beta dispersion (usually although not exclusively around 50 MHz). Components 48 and 49, 51 and 52, 47/49 and 58 operate exactly as in accordance with the equivalent components in the voltage monitoring system described in FIG. 6.

In the case of blood, the detected voltage is related to the total protein content being mainly haemoglobin and fibrinogen. Frequency $f_1$ lies between the alpha and beta dispersions and components 45, 46, 50 and 54 operate exactly as in accordance with their equivalent counterparts in the kilohertz frequency recovery method described by reference to FIG. 7. However, an extra component takes the form of a series quartz crystal or similar filter 56 to remove any traces of high frequency signal which may have strayed into this part of the circuit where it is unwanted. The voltage at the detector 57 is related to the number density of erythrocytes, if sample is blood, and this number density in turn correlates to a large extent with sample haemoglobin content, for the vast majority of pathological samples.

The voltage at detector 57 is also weakly dependent on haemoglobin concentration direct and also on mean cell volume according to a complex mathematical function involving both. Thus appropriate mathematical manipulation of the signals from detectors 57 and 58 in circuit 59 (at its simplest comprising two operational amplifiers) can remove an approximate contribution due to haemoglobin from the total protein function, to leave remaining a signal contribution which depends mainly on fibrinogen levels. The output scale factor may be arranged to yield a novel output parameter which the present inventor chooses to refer to as the ISR (instant sedimentation rate) namely a non-time-dependent parameter from which a value which correlates with time-dependent ESR can be derived by calculation and displayed by suitably scaling the display device in magnitude and dynamic range according to the more traditional ESR a parameter which physicians are more used to interpreting.

Those skilled in the art however will appreciate that there is no reason why the output should not be scaled in order to give an "instant" PV reading or an "instant" CRP reading covering the equivalent dynamic ranges of these two parameters and indeed this is within the scope of the present claims herein.

Figure 14:
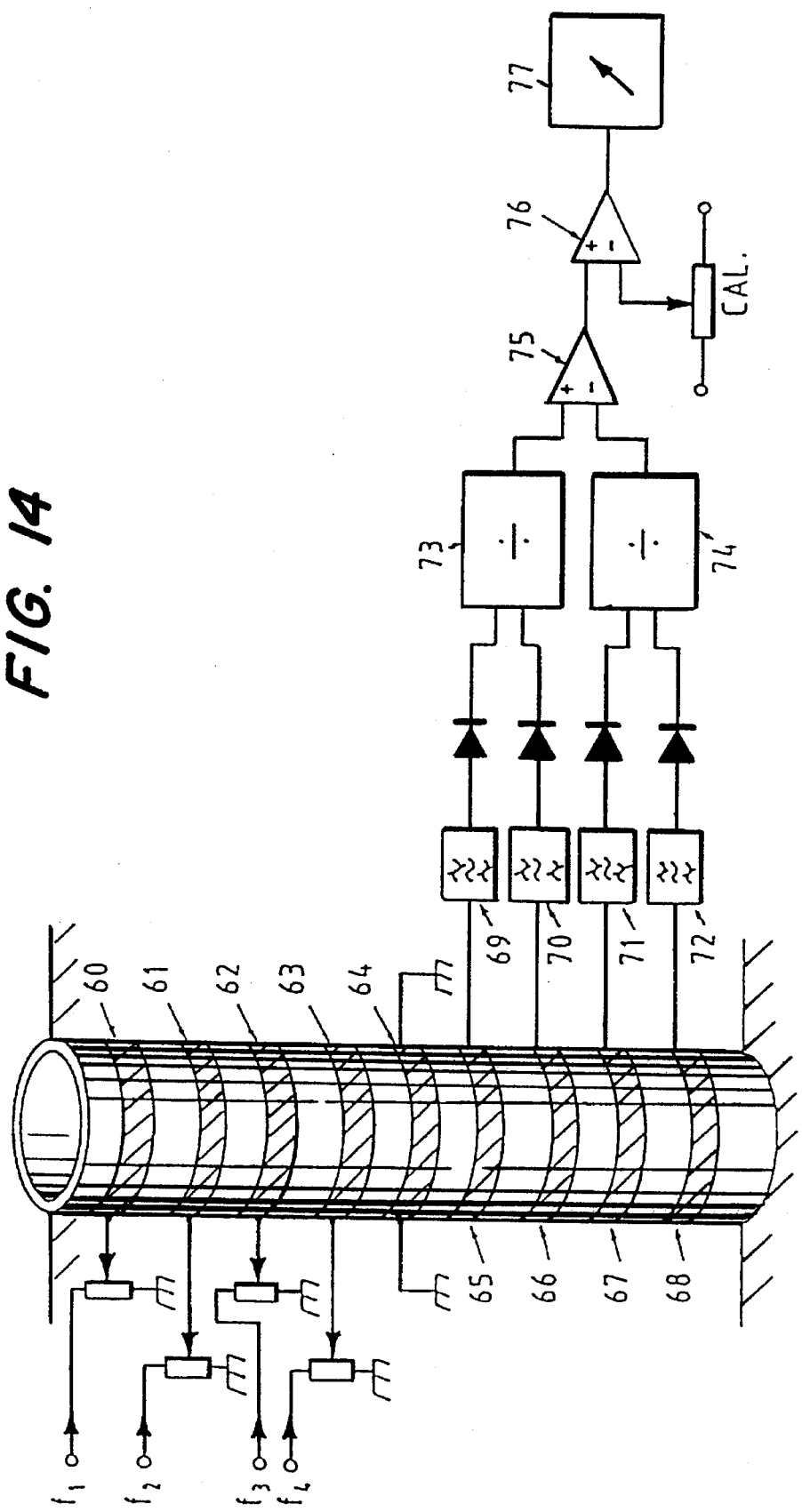
FIG. 14 illustrates a four frequency method and device for the measurement of protein, preferably fibrinogen in blood according to this invention.

Referring next to FIG. 14, this illustrates a block diagram of the four frequency cell, measurement method and device for use with this aspect of the present invention. Because different parts (in frequency space) of the high frequency tail of the dielectric beta dispersion are influenced in different ways by different proteins, e.g. haemoglobin and fibrinogen, if the sample is blood, it is possible to obtain an estimate of fibrinogen levels by simultaneous four frequency dielectric measurement in the frequency range 15–60 MHz (usual but not exclusive range within scope of aspect of the this present invention). Usually frequency $f_1$ is of the order of 17 MHz, $f_2$ is of the order of 20 MHz, $f_3$ is of the order of 30 MHz, and $f_4$ is of the order of 50 MHz.

Frequencies $f_1$–$f_4$ are passed in through electrodes 60–63 and out through electrodes 65–68 inclusive. Narrow bandpass filters 69–72 centred on $f_1$–$f_4$, respectively assist; with signal recovery. An analogue divider 73 divides the detected voltage from the 17 MHz filter and detector by the voltage derived from the MHz signal 20. Likewise, divider 74 performs a similar operation for $f_3/f_4$. For blood as a sample, output functions of dividers 73 and 74 have similar components in respect of haemoglobin but somewhat different for fibrinogen, then weighted subtraction in processor 75 tends to enhance the effect of fibrinogen and suppress the effect of haemoglobin.

At this point in the circuit the fibrinogen function is almost linear but is superimposed on a d.c. lend. Thus, an appropriate offset is provided by processor 76 so that the output parameter may be indicated on display 77. Those skilled in the art will appreciate that the technique is not limited within the scope of the claims to only blood as a sample and indeed any system containing cellular biomass and protein together or even mixtures of proteins will be amenable to this kind of treatment. When the sample is blood, this aspect of the invention is a most accurate way of determining fibrinogen but because four frequencies are employed, very careful adjustment and initial calibration initially with pathological samples and latterly with electrolyte solutions is necessary and temperature compensation of components 73–76 is also desirable.

Figure 15:
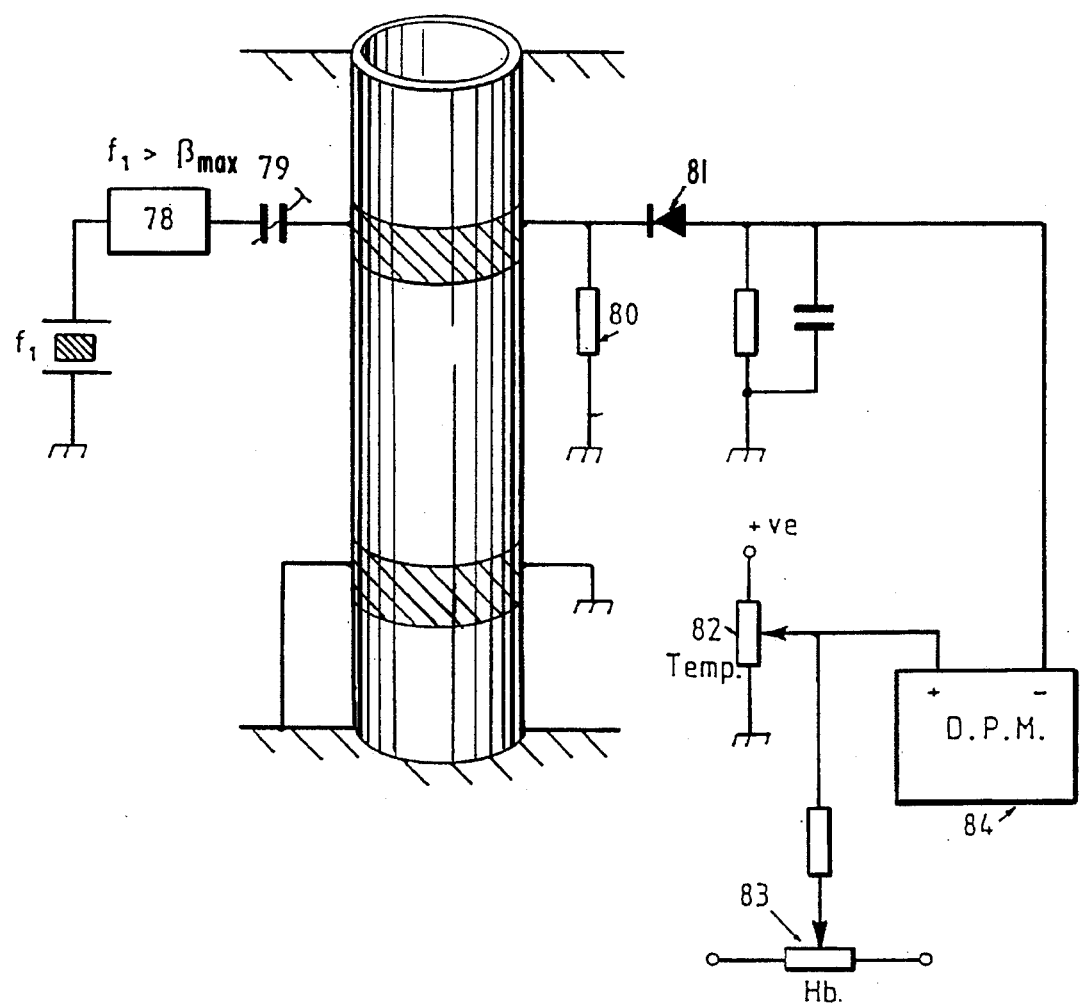
FIG. 15 illustrates a single frequency device used in conjunction with an external entry parameter to yield a new parameter, where the entry parameter is preferably haemoglobin content, to yield fibrinogen content or a related parameter, at an output if the sample is blood.

Referring next to FIG. 15, the block diagram illustrates the aspect of the invention concerned with fibrinogen or protein assessment when a numeric entry parameter (e.g. haemoglobin) is available or known. If haemoglobin content of blood is known or available from another source such as a Coulter or similar cell counter or biochemical optical haemoglobinometer, and is used as an external entry parameter, the invention according to this aspect can be used to provide a simpler and more accurate assessment of fibrinogen level. Referring then to the drawing, the main component parts 78–81 of the system operate in exactly the same accord as their equivalent parts indicated in FIG. 6.

The digital voltmeter 84 is used with a differential input and temperature is compensated for using potentiometer 82. Those skilled in the art will appreciate automatic compensation also to be possible within the scope of the present claims. The haemoglobin entry circuit 83, is also shown for simplicity as a potentiometer, but may in practice be comprise of a set of rocker or thumbwheel type switches and it is usually adequate to enter the haemoglobin value to the nearest whole unit. Those skilled in the art will appreciate that there are several other means of haemoglobin entry, both analogue and digital within the scope of the claims of this present invention, including for example acquisition of the haemoglobin level by direct connection to the electronic circuitry of a cell counter or haemoglobinometer.

The action of the system is achieved because the voltage 81 at detector is an inverse function of the total protein content and the differential action of voltmeter 84 removes from this the haemoglobin contribution and simultaneously allows addition of the temperature compensation voltage. Those skilled in the art will appreciate that the invention according to this aspect could be used with multi-component fluid systems other than blood within the scope of the claims of this invention, and that if a manually acquired ESR, value were available, instead of haemoglobin, the system could be configured "in reverse" to yield a haemoglobin value at its output within the scope of these present claims.

Those skilled in the art will appreciate that simultaneous frequencies may be applied through just one electrode or inductor, within the scope of the claims of this present invention by using power combiners and/or directional coupling techniques.

it will be understood that when employing any of the cells, means, methods and devices referred to in this present embodiment, and by way of reference to the drawings, if the sample is provided in its own container, the container being a tube, vacutainer, capillary etc. with open or sealed end(s), such container should be a snug push fit into former/tube of the cell of FIGS. 5–14, and there should not be excessive slack or excess air gap (although not all the air is displaced) between this container and the inner walls of the former.

If the container dimensions vary (from container to container), particularly the internal and external diameters, then errors in the measurement produced by methods and devices herein may arise. Such errors arise from variations in the air gap capacitance where the air gap is that between the container and former.

It will, however, be appreciated by those skilled in the art that such errors can be reduced/corrected for manually or automatically by tube size correction techniques.

Furthermore they will appreciate that this problem may be turned on its head to yield yet a further aspect of the invention referred to above and in the claims herein, namely that if samples of fixed chemical and dielectric property are employed in sample containers of nominally the same size but with slight variations in size or dielectric property, then the cells, methods, means and devices may be used to measure a physical dimension of the sample container without the use of a rule, callipers, micrometer other gauges or optics.

Figure 16:
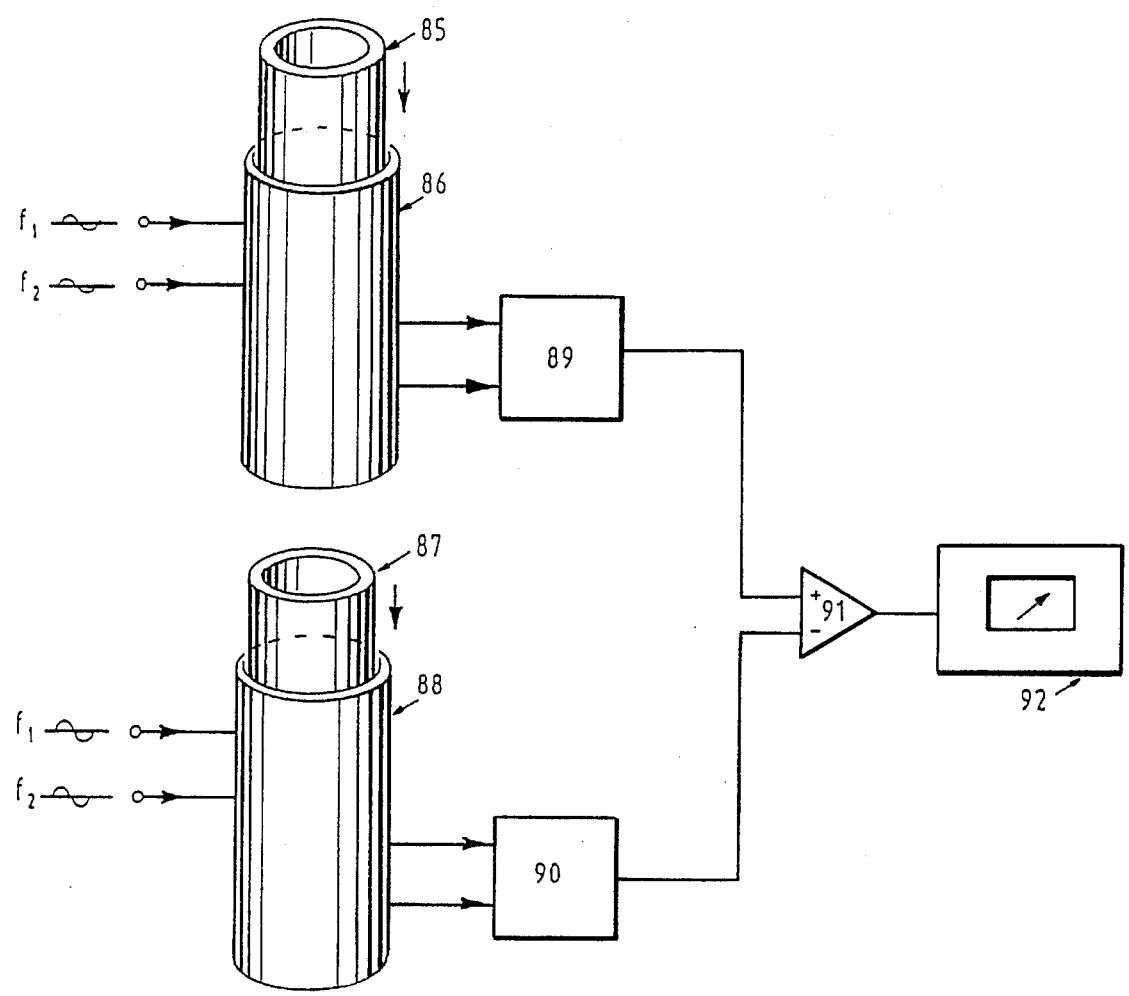
FIG. 16 illustrates the differential mode, according to this invention.

Referring finally to FIG. 16 a sample tube 85 and a dummy or control sample tube 87 are inserted in identical formers 86 and 88 of the kind as illustrated in any of FIGS. 5 to 15. Identical electronic circuits 89 and 90 are associated with any of the means, methods and devices according to this invention such a difference amplifier 91 and an appropriately scaled output device/display 92. Effects of temperature and other environmental factors tend to be cancelled by this arrangement, thus making the invention according to this aspect more stable and accurate than those previous disclosures which do not employ a differential mode.

Figure 17:
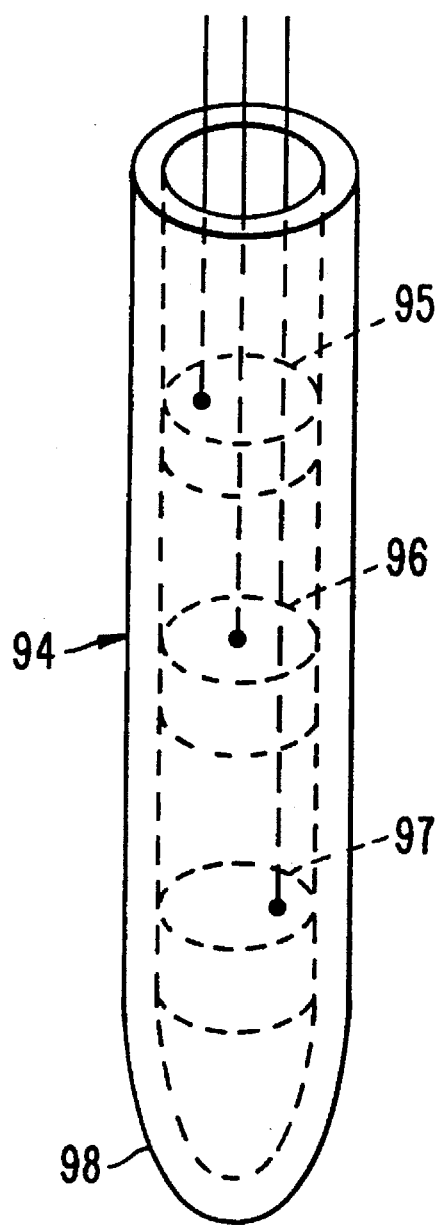
FIG. 17 illustrates an alternative form of the apparatus in accordance with the present invention, showing a probe for insertion into a sample of fluid under investigation.

Throughout this description, the sample by way of example has been considered to be substantially static and in a closed or open ended sample tube. However, the sample may be a flowing or moving sample, in which case the formers referred to in every aspect herein would then be of the variety with both ends open. Furthermore, it will be appreciated by those skilled in the art, that the aforesaid formers could be fabricated in a "turned inside out" manner, as illustrated in FIG. 17 with electrodes or inductors 95, 96, 97 disposed on the inside of a hollow probe 94 with a closed end 98 to prevent fluid entry or contact with the electrodes or inductors, thus forming the probe 94 which could then be dipped into samples otherwise retained, but yet with operation in accordance with the claims of this present invention.

Furthermore, those skilled in the art will appreciate that all the cells, methods, means and devices referred to herein may be provided with manual or automatic means of sample mixing, handling, labelling etc; and results, analogue or digital, could also be computer stored or on a prim-out, and samples may or may not be aspirated from their original containers into second or subsequent containers.

Furthermore, nothing in this present invention prevents the sample from being biomaterial in vivo i.e., small cells or large human body digits, limbs etc.

Furthermore, those skilled in the art will appreciate that there is scope for modification in the aspects of the embodiments that refer to simultaneous multi-frequency excitation and reception since digital as well as analogue methods can be used here and pseudo instantaneous output may be obtained by using fast frequency steps or sweeps of frequencies applied to transmit electrodes. Further in all aspects where diode detection is employed within the present embodiment, see particularly FIGS. 6 and 7 and FIGS. 10–13, this can be replaced by phase sensitive detection as a viable alternative with the dual consequence of added sensitivity and two component information from the real and imaginary part analysis, advantageous since in reality samples exhibit complex dielectric behaviour and dielectric constant, sometimes referred to as permittivity has such real and imaginary parts.

For a sample dielectric property the present inventor states the real part permittivity is a measure of the sample a.c. capacitance and with the present invention the apparatus using circumferential electrodes will respond mainly to this capacitive facet, whereas coils will respond more strongly to the imaginary part of the permittivity (loss) or conductive facet.

What is claimed is:

1. A method for investigating one or more parameters of biofluids, particularly blood in respect of protein and cellular concentrations and cellular volume, comprising the steps of: applying to a sample of the biofluid and without direct contract with the sample at least two a.c. frequencies in a range of 0.1 to 60 MHz; simultaneously receiving and resolving said frequencies after their passage through said fluid; obtaining subsequent d.c. voltage amplitudes by detection of said received and resolved frequencies; thereafter applying mathematical processing to said d.c. voltage amplitudes to provide a numeric output which correlates with at least one of said parameters.

2. A method as claimed in claim 1, wherein said two frequencies form a pair within a recognised frequency dispersion, and at least one of the frequencies is close to a maximum amplitude of said dispersion.

3. A method as claimed in claim 2, wherein both of said frequencies offset to a same side of the peak frequency.

4. A method as claimed in claim 2, wherein the biofluid is blood and the pair of frequencies is within a beta dispersion, the parameter under determination being the mean cell volume (MCV).

5. A method as claimed in claim 4, wherein the pair of frequencies is on a low frequency side of a dispersion peak frequency.

6. A method according to claim 5, wherein the frequency pair is in a range of 1.5 to 2.6 MHz.

7. A method as claimed in claim 2, wherein the biofluid is blood and the pair of frequencies is within a beta-1 dispersion, the parameter under determination being haemoglobin level (Hb).

8. A method according to claim 7, wherein the pair of frequencies is on a high frequency side of a dispersion peak frequency.

9. A method according to claim 8, wherein the frequency pair is within a range of 14 to 22 MHz.

10. A method as claimed in claim 2, wherein the biofluid is blood and the pair of frequencies is within a delta dispersion, the parameter undergoing determination being the total protein content.

11. A method as claimed in claim 10, wherein fibrinogen level is determined by subtracting haemoglobin level from a total protein content value.

12. A method as claimed in claim 11, wherein the pair of frequencies is within a beta -1 dispersion which is used to determine haemoglobin level.

13. A method as claimed in claim 11, wherein the haemoglobin level is determined separately and inputted manually.

14. A method as claimed in claim 11, wherein the parameter under determination is instantaneous sedimentation rate (ISR).

15. A method as claimed in claim 2, wherein said mathematical processing includes a division of one of said d.c. voltage amplitudes by the other of said d.c. voltage amplitudes.

16. A method as claimed in claim 2, wherein said mathematical processing includes a subtraction step in respect of one of said parameters.

17. A method as claimed in claim 1, wherein the biofluid is blood and said one or more parameters are chosen from haemoglobin content, red cell count, mean cell volume, total protein content, fibrinogen level and fibrinogen level scaled in terms of instant sedimentation rate (ISR).

18. A method as claimed in claim 1, wherein said a.c. frequencies are each stable and of non-varying amplitude and frequency.

19. An apparatus for obtaining a numeric output which correlates with at least one or more parameters of a biofluid, said parameters including protein and cellular concentrations and cellular volume of blood, the apparatus comprising: a measurement cell for containing a sample of a biofluid; means for applying a signal having at least two a.c. frequencies in a range of 0.1 to 60 MHz to the said sample of the biofluid within said cell and without direct contact with the sample; means for receiving and resolving said signal having at least two a.c. frequencies after passage through said sample of biofluid; means for obtaining d.c. voltage amplitudes by detection of said received and resolved signal having at least two a.c. frequencies; and means for applying a mathematical processing to said obtained d.c. voltage amplitudes to provide said numeric output which correlates with at least one of said one or more parameters of the biofluid.

20. Apparatus according to claim 19 wherein, said means for applying and receiving said two or more frequencies are arranged externally of said cell.

21. Apparatus as claimed in claim 19, wherein said means for applying and receiving said two or more frequencies are disposed within a probe which inserted into a sample in said cell.

* * * * *